(12) United States Patent
Park

(10) Patent No.: US 6,461,666 B2
(45) Date of Patent: Oct. 8, 2002

(54) RADIOACTIVE BALLOON FOR DILATION CATHETER SYSTEM AND PROCESS FOR PREPARATION THEREOF

(75) Inventor: Kyung Bae Park, Taejon-si (KR)

(73) Assignee: Korea Atomic Energy Research Institute, Taejon-si (KR)

( * ) Notice: Subject to any disclaimer, the term of this patent is extended or adjusted under 35 U.S.C. 154(b) by 0 days.

(21) Appl. No.: 09/780,140

(22) Filed: Feb. 9, 2001

(65) Prior Publication Data

US 2001/0007916 A1 Jul. 12, 2001

Related U.S. Application Data

(62) Division of application No. 09/131,911, filed on Aug. 10, 1998, now abandoned.

(30) Foreign Application Priority Data

Dec. 24, 1997 (KR) .............................................. 97-73441

(51) Int. Cl.[7] .......................... A61L 27/00; A61L 29/00; B05D 1/18
(52) U.S. Cl. ...................... 427/2.28; 427/2.1; 427/2.24; 427/2.25; 427/430.1; 427/435
(58) Field of Search .................................. 427/2.1, 2.24, 427/2.25, 2.28, 430.1, 435

(56) References Cited

U.S. PATENT DOCUMENTS

| | | | | |
|---|---|---|---|---|
| 4,377,567 A | * | 3/1983 | Geho | 424/1.21 |
| 5,782,742 A | * | 7/1998 | Crocker et al. | 600/3 |
| 5,977,163 A | * | 11/1999 | Li et al. | 424/1.65 |
| 6,103,295 A | * | 8/2000 | Chan et al. | 427/346 |
| 6,149,574 A | * | 11/2000 | Trauthen et al. | 600/3 |
| 6,162,165 A | * | 12/2000 | Apple et al. | 600/3 |
| 6,264,596 B1 | * | 7/2001 | Weadock | 600/3 |
| 6,287,249 B1 | * | 9/2001 | Tam et al. | 600/3 |

* cited by examiner

*Primary Examiner*—Shrive P. Beck
*Assistant Examiner*—Jennifer Kolb Michener
(74) *Attorney, Agent, or Firm*—Bachman & LaPointe, P.C.

(57) ABSTRACT

The present invention relates to a radioactive balloon for angioplasty which is combined with a flexible film containing radionuclides and process for preparation thereof. A balloon dilatation catheter system containing the radioactive balloon can be used in transluminal coronary angioplasty, expanding blood vessel and facilitating the blood flow so as to prevent the proliferation of smooth muscle cell and vascular restenosis efficiently.

2 Claims, 2 Drawing Sheets

RADIOACTIVE BALLOON FOR DILATION CATHETER SYSTEM AND PROCESS FOR PREPARATION THEREOF

CROSS-REFERENCE TO RELATED APPLICATION

This application is a divisional of U.S. patent application Ser. No. 09/131,911, filed Aug. 10, 1998, now abandoned.

FIELD OF THE INVENTION

The present invention relates to a radioactive balloon for angioplasty which is combined with a flexible film containing radionuclides and process for preparation thereof, which can prevent vascular restenosis efficiently.

BACKGROUND OF THE INVENTION

Percutaneous transluminal coronary angioplasty has been operated to treat coronary-stenosing diseases such as arteriosclerosis and the like. The angioplasty was first performed in human body by Gruenzig et al. in 1977 and has been firmly established as a curative method for treating coronary diseases. Presently, 500,000 people per year have been reported to be treated with the method worldwide (Holmes, D. R. et al., Am. J. Cardiol., 53: 77C–81C, 1984). In Korea the angioplasty has also been performed actively, especially at the university hospitals.

Since operational apparatuses for the percutaneous transluminal coronary angioplasty were developed diversely, the angioplasty has been widely performed so as to be applied to various diseases. Practically, the angioplasty has been operated in single vessel disease and multiple vessel disease, stable angina pectoris and instable angina pectoris, acute myocardial infarction and the like (Nobuyoshi, M. et al., J. Am. Coll. Cardiol., 17: 198B, 1991; Waller, B. F. et al., J. Am. Coll. Cardiol., 17: 58B–70B, 1991).

Although the angioplasty treated by using the balloon dilatation catheter, etc. succeeded clinically at the rate of 95%, but acute closure and restenosis can be induced before and after the operations.

The restenosis described above may be induced by the mechanisms such as the vascular remodeling, the proliferation of the injured smooth muscle cell (SMC), the formation of extracellular matrix and the like (Wither, H. R. et al., Cancer, 34: 39–47, 1974; Thames, H. D. et al., Int. J. Radiat. Onco. Biol. Phys., 7: 1591–1597, 1981). Although the smooth muscle cell within the vessel is not proliferative normally, physical defects and stimuli incites smooth muscle cell to migrate into the inner layer of blood vessel, to multiply or to form a matrix tissue.

In early days of coronary angioplasty, such a restenosis occurred in approximately 30–45% of patients. New methods such as atherectomy, rotabulation, use of transluminal extraction catheter (TEC), excimer laser coronary angioplasty and insertion of stent have been accomplished in order to reduce the restenosis rate.

The above methods were also performed clinically by using anti-thrombocyte agent, anti-coagulant, steroids, calcium channel blocker, colchicine, etc. in order to prevent the restenosis. But effective drugs reducing the restenosis has not yet been discovered. Recently, local drug delivery and gene therapy also are being performed a lot, which shows good effects in in vitro study, but the effects were uncertain in in vivo study. Since blood flows through the blood vessel fast and washes off the above drugs, such a treatment is not effective. Especially, it is more difficult to administer the drugs at the specific sites of the blood vessel.

As described above at the restenosed sites, lesions of the blood vessel also induces neointimal hyperplasia. In this case, local radiation can decrease the number of progenitor cells in regenerating tissues.

It is reported that ionizing radiation inhibits the thymidine uptake and the collagen synthesis in cultured fibroblast and can be used effectively at a low dosage for preventing proliferative lesions or keloids which are formed after the surgical operation. At that time, about 10 Gy (1,000 rad) of radiation may be irradiated for the treatment, which does not affect the general treatment process.

Practically, the insertion of metallic stent is a general method to prevent the restenosis which is induced after operating the transluminal coronary angioplasty in artery-restenosing diseases. In place of the simple metallic stent, radioactive stents coated with radionuclides such as Ir-192, Y-90, P-32 and the like have been developed to inhibit the proliferation of smooth muscle cell fundamentally. Radioactive rays emitted from the stents destruct the multiplying cells, and this is exploited to prevent the restenosis actively.

However, after the insertion of the stent, the amount of radioactivity can not be adjusted according to the change of the patient's state. In order to settle the shortcomings, a minimally invasive medical device for providing the radiation treatment has been designed (U.S. Pat. No. 5,484,384). Precisely, the medical device comprises a outer sheath, a wire coil and a flexible elongated member having distal and proximal portion which can slide through the sheath. The device also contains radioactive isotopes at the elongatable distal portion and can be utilized for the radiation therapy controlling the radioactivity.

In addition, an invasive medical device has been designed, which is combined with a sleeve containing radioactive isotopes which is dispersed and adhered onto the wire coil. In detail, the device comprises an elongatable distal portion, an expandable balloon and a catheter and can irradiate the wall of the blood vessel wall by expanding the wall of the balloon with radioactive liquid instead of gas (Fearnot, U.S. Pat. No. 5,484,384, 1996).

In order to irradiate a lesion site evenly, radioactive material should fill the balloon for expanding. However, when the balloon ruptures during the angioplasty, radioactive material may be absorbed into human body which causes serious danger. When beta-ray emitting nuclides are used, the restenosing site in the blood vessel wall can be irradiated only by radioactive material which is in contact with the surface of the inner space of the balloon since it has a short transmitting distance. Thus other radioactive materials within the inner space of the balloon can not be utilized for the irradiation and are lavished on the expansion only.

In order to settle the shortcomings, a balloon dilatation catheter system consisting of 2 balloons has been developed. In the catheter system, an inner balloon is used to expand the system and an outer balloon, to fill the radioactive material (such as I-125, P-32), so as to reduce the lavished radioactivity and improve safety problems (Bradshaw, et al., U.S. Pat. No. 5,662,580, 1997). In addition, a balloon dilatation catheter system which exploits radioactive capsule or pellet, suspended in liquid for filling the balloon has been established for the radiation therapy (Waksman, et al., U.S. Pat. No. 5,683,345, 1997).

However, radioactive balloon dilatation catheter system with 2-layered balloons or the system including radioactive capsule or pellets are both not safe when the outer balloon is disrupted. The disruption releases radioactive material into the body and so it gets irradiated. Furthermore, the process for preparing the catheter system is too difficult and complex to be performed.

Therefore, in order to overcome the above problems of the general radioactive balloon, the present inventors have developed new balloon dilatation catheter system which can prevent the restenosis efficiently after the transluminal coronary angioplasty. To be precise, radioactive balloon used in this catheter system has been prepared by mixing radionuclides with carrier material, immersing the balloon into the mixed solution and drying it so as to produce the balloon surface coated with radioactive film. The balloon dilatation catheter system exploiting the balloon inhibits the restenosis in vascular restenosing diseases effectively.

SUMMARY OF THE INVENTION

The object of the present invention is to provide a radioactive balloon of balloon dilatation catheter which is surrounded with a flexible film containing radionuclides for preventing restenosis after the treatment of vascular restenosing diseases.

The present invention provides a radioactive balloon which is surrounded with a flexible film containing radionuclides and used in balloon dilatation catheter.

The present invention provides the radioactive balloon which utilizes Sm-153, Dy-165, Ho-166, Er-169, P-32, Y-90, I-131, Re-186, Re-198, Pd-109 or Au-198 as beta-ray emitting nuclide and Ir-192, Co-57, Co-60, V-48 or I-125 as gamma-ray emitting nuclide.

The object of the present invention is to provide processes for preparing the radioactive balloon.

The present invention provides a process for preparing the radioactive balloon which comprises;

(S1) immersing the balloon of the balloon dilatation catheter in solution containing radionuclide compound, and (S2) maintaining the above balloon in a horizontal position and drying it to form a film layer.

The present invention provides uses of the balloon dilatation catheter containing the radioactive balloon for treating the angiostenosis found in vascular disease such as arteriosclerosis.

Figure 1:
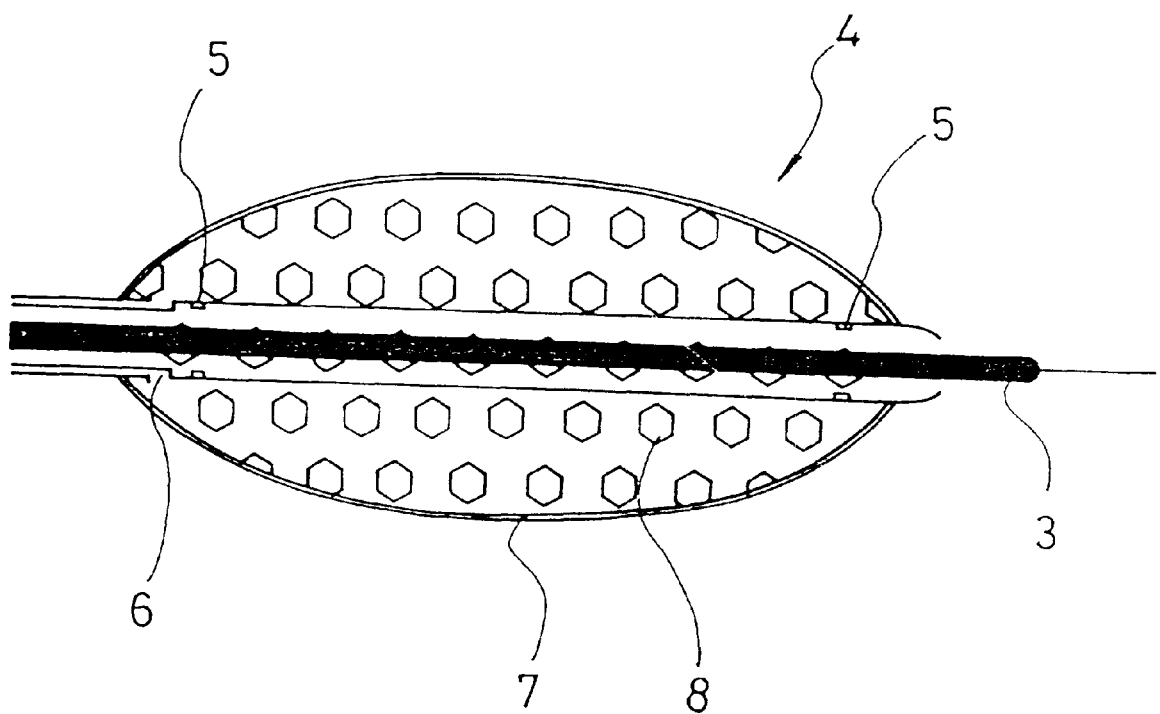
FIG. 1 depicts a portion of a vertical sectional view of the radioactive balloon used in a radioactive dilatation catheter system which is in the expanded state.
Figure 2:
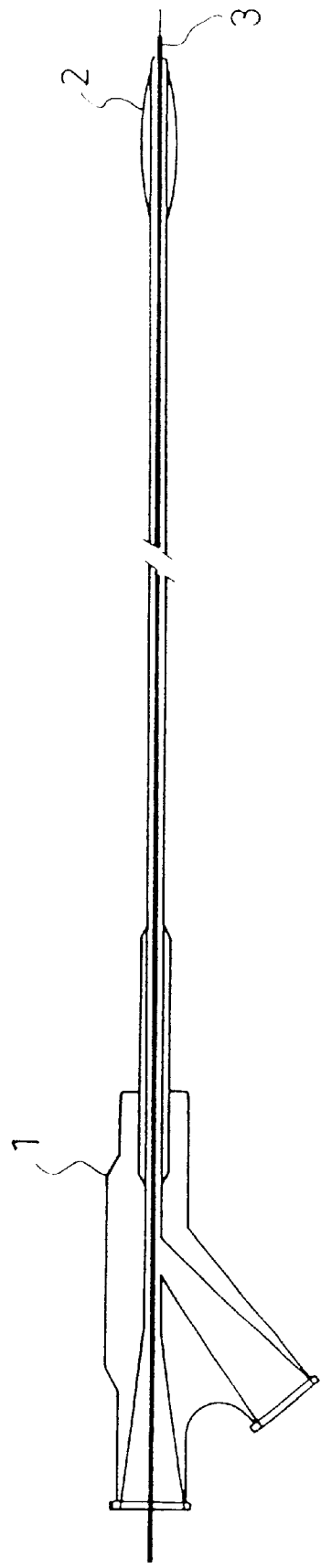
FIG. 2 depicts a vertical sectional view of general balloon and its delivery system commercially available.

1 : delivery system; 2 : balloon; 3 : guiding wire; 4 : radioactive balloon; 5 : balloon marker; 6 : air inflow opening; 7 : radioactive film surrounding the balloon; 8 : radioactive nuclides contained in the film

DETAILED DESCRIPTION OF THE INVENTION

Referring to the drawings, the radioactive balloon for angioplasty will be described detaily as follows.

Figure 3:
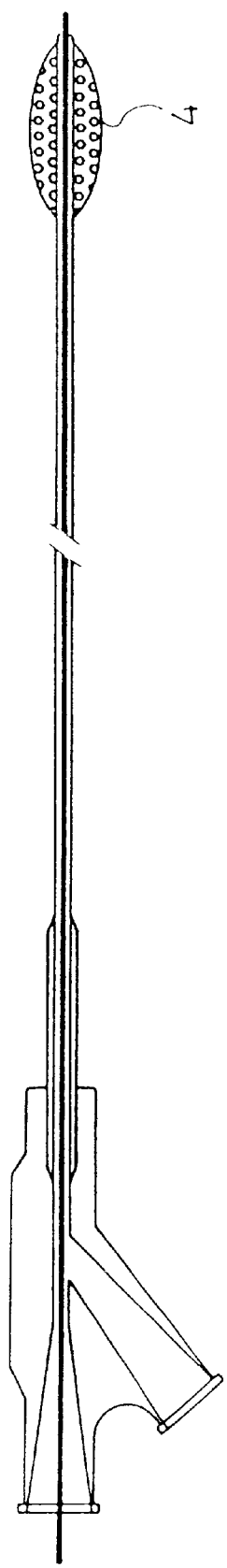
FIG. 3 depicts a vertical sectional view of the balloon and its delivery system of the present invention.

The radioactive balloon of the present invention is made of radioactive film (7) and attached to end of guiding wire (3) in an ellipsoidal form as described in FIGS. 1 and 3 No. 3. This balloon (4) is formed into a flat film while migrating in the body and expands at the lesion site by enhalating air through air inflow opening (6) as shown in FIG. 1 so as to prevent restenosis.

In this case, the radioactive film (7) surrounding the outer surface of the balloon (4) contains radioactive nuclides (8) which are dispersed within the film evenly, thus gamma- or beta-rays and both the rays emitted from the radionuclides (8) disrupts smooth muscle cells efficiently for preventing cell proliferation and restenosis of the treated lesion site in vascular restenosing diseases.

In this case, Sm-153, Dy-165, Ho-166, Er-169, P-32, Y-90, I-131, Re-186, Re-188, Pd-109 or Au-198 are utilized preferably as beta-ray emitting nuclide. Ir-192, Co-57, Co-60, V-48 or I-125 as gamma-ray emitting nuclide and Pd-103 as both gamma- and beta-ray emitting nuclide can be utilized. In addition, most radionuclides used for therapeutic nuclides can be exploited in preparing the above radioactive balloon for the balloon dilatation catheter of angioplasty.

The radioactive balloon (4) of the present invention is made of elastic and expandable polymer. The above balloon can be prepared as various forms according to size and shape and can be used widely for preventing the restenosis in vascular restenosing diseases such as arteriosclerosis and inhibiting cell propagation.

The present invention provides processes for preparing the radioactive balloon of the balloon dilatation catheter system.

The radioactive balloon (4) is prepared by the process which comprises;

(S1) immersing the balloon of the balloon dilatation catheter in a solution containing a radionuclide compound, and (S2) maintaining the above balloon in a horizontal position and drying it to form a film layer.

In step (S1) a radionuclide compound emitting radioactive rays is utilized in order to prepare the radioactive balloon for the angioplasty. Particularly, the radionuclides is mixed well with the above carrier material and dried so as to be dispersed evenly and fixed within the carrier polymer to prevent them from flowing outwardly. Since the above radioactive balloon prepared are combined with the film tightly, an adhesive agent for preventing separation is not needed.

The process of this invention will be described detaily as follows.

In detail, a radioactive nuclide compound and carrier material are dissolved in the mixed solvent of dimethylformamide (DMF) and tetrahydrofurane (THF) and the balloon of the balloon dilatation catheter is immersed into the above solution directly, dried to form the radioactive film attached onto the balloon. As a result, the balloon coated with radioactive film is produced.

In the above process it is preferable that polyurethane, latex or butyl rubber polymer be utilized as a carrier material. And it is appropriate for the film's thickness to be 40–100 μm. Besides, acryl series, chloroprene series, PVA series, nylon series or the like can be utilized.

The radioactive balloon of the present invention also can be prepared by the process which comprises;

(S1) preparing the film by mixing a radionuclide compound with carrier material, (S2) surrounding a non-radioactive balloon with the above film, and (S3) adhering the film onto the above balloon.

At that time it is preferable that epoxy adhesive agent is utilized.

A radioactive balloon dilatation catheter system is prepared by assembling the above radioactive balloon.

The above balloon dilatation catheter can be used in transluminal coronary angioplasty so as to expand blood vessel for facilitating the blood flow and so as to prevent the proliferation of smooth muscle cell and vascular restenosis efficiently.

Practical and presently preferred embodiment of the present invention are illustrated as shown in the following Examples.

However, it will be appreciated that those skilled in the art, on consideration of this disclosure, may make modification and improvements within the spirit and scope of the present invention.

EXAMPLES

Example 1
Preparation of the radioactive balloon containing Ho-166

In order to prepare the radioactive balloon for the angioplasty containing radionuclides, $^{165}Ho(NO_3)_3 \cdot 5H_2O$ was irradiated with neutrons in the nuclear reactor and converted to $^{166}Ho(NO_3)_3 \cdot 5H_2O$.

2.4 g of $Ho(NO_3)_3 \cdot 5H_2O$ and 2.4 g of polyurethane(PU) were completely dissolved in mixed solvent of 4 ml of dimethylformamide (DMF) and 40 ml of tetrahydrofurane (THF) at room temperature. A balloon was immersed in the solution containing PU and taken out. After 3 hours the THF solvent which is highly volatile was evaporated and then the film layer containing radionuclides was produced.

The radioactive balloon prepared as above was connected to the balloon dilatation catheter in order to produce the radioactive balloon dilatation catheter.

As described above, the radioactive balloon dilatation catheter system of the present invention is combined with the radioactive balloon coated with elastic and flexible film containing radioactive material. Therefore the catheter system prevents the inflow of radioactive material into the body and body irradiation fundamentally. And unnecessary radiation to the patient or workers can be reduced since a minimal amount of radioactivity is coated onto the balloon. Besides, in case of using beta-ray emitting nuclides having shorter transmitting distance rather than gamma-ray emitting nuclides the treatment results is efficient since lesion sites can be irradiated directly and at the closest position.

In addition, the process for preparing the radioactive balloon is much easier than that of a general balloon which exploits radioactive liquid material, capsule or the like so that the efficiency of producing the balloon is highly increased.

Therefore, the radioactive balloon of the balloon dilatation catheter system can be used in the transluminal coronary angioplasty, expanding blood vessel and facilitating the blood flow and preventing the proliferation of smooth muscle cell and vascular restenosis efficiently.

What is claimed is:

1. A process for preparation of a radioactive balloon which comprises;

(1) immersing a balloon into a solution containing a $Ho(NO_3)_3 5H_2O$ radionuclide and a carrier material which is selected from the group consisting of polyurethane, latex and butyl rubber, (2) removing and maintaining the balloon in a horizontal position, and (3) drying the balloon to form a film layer thereon having a thickness of between 40–100 microns.

2. The process for preparation of the radioactive balloon according to claim 1, wherein the radionuclide of step (1), is a radionuclide compound.

* * * * *